United States Patent [19]
Henshall et al.

[11] Patent Number: 5,936,119
[45] Date of Patent: Aug. 10, 1999

[54] CHEMICAL PROCESS

[75] Inventors: John Barry Henshall, Urmston; John Whitworth, Audenshaw, both of United Kingdom

[73] Assignee: Ciba Specialty Chemicals Corporation, Tarrytown, N.Y.

[21] Appl. No.: 09/014,373

[22] Filed: Jan. 27, 1998

[30] Foreign Application Priority Data

Jan. 28, 1997 [GB] United Kingdom .................. 9701667

[51] Int. Cl.⁶ .................................................. C07C 229/60
[52] U.S. Cl. ........................................... 562/458; 562/433
[58] Field of Search ...................... 562/433, 458

[56] References Cited

U.S. PATENT DOCUMENTS 4,233,458   11/1980   Bright et al. ............................ 562/458

FOREIGN PATENT DOCUMENTS 2930616   2/1980   Germany .
1462258   1/1977   United Kingdom .

OTHER PUBLICATIONS

Database CAPLUS on STN, Acc. No. 1991:81171, Wen et al., 'Preparation of meta-(dimethylamino)benzoic acid.' Huaxue Shiji (1990), 12(4), p. 243, abstract.
Derwent Abst. 77-53156y.
Chem. Abst. 120:133965m.

*Primary Examiner*—Gary Geist
*Assistant Examiner*—Brian J. Davis
*Attorney, Agent, or Firm*—Kevin T. Mansfield

[57] ABSTRACT

The invention provides a process for the preparation of 3-(N,N-dimethylamino)benzoic acid which comprises subjecting an aqueous solution of an alkali metal salt or ammonium salt of 3-aminobenzoic acid to reductive methylation in the presence of a supported transition metal catalyst, by the controlled and continuous addition of a solution of formaldehyde over a period of 0.5 to 20 hours with a hydrogen pressure between 1 bar and 40 bar and with the temperature of the reaction mass gradually raised during the reduction, the reaction being carried out within the temperature range of 20° C. to 120° C., and wherein a buffering agent is added such that the pH of the reaction mass after reductive methylation is from 6.5 to 9.5.

9 Claims, No Drawings

CHEMICAL PROCESS

This invention relates to a method of producing 3-(N,N-dimethylamino)benzoic acid.

3-(N,N-dimethylamino)benzoic acid is a key intermediate for the preparation of 3,3-bis[4-(N,N-dimethylamino) phenyl]-6-N,N-dimethylamino-phthalide, a dyestuff used in pressure- or heat-sensitive recording systems.

The importance of 3-(N,N-dimethylamino)benzoic acid in the manufacture of 3,3-bis[4-(N,N-dimethylamino) phenyl]-6-N,N-dimethylamino-phthalide, also known as Crystal Violet Lactone, has led to a large number of manufacturing procedures.

One approach to the manufacture of 3-(N,N-dimethylamino)benzoic acid is by alkylation of 3-aminobenzoic acid with an alkylating agent such as a methyl halide or dimethyl sulphate. A disadvantage of this approach is the toxic nature of the alkylating agents.

Of particular importance in recent years is the method of reductive alkylation accomplished by reacting 3-aminobenzoic acid with formaldehyde in the presence of hydrogen and a noble metal catalyst. The 3-aminobenzoic acid may be produced in situ by catalytic hydrogenation of 3-nitrobenzoic acid.

As an illustration of the reductive alkylation route to 3-(N,N-dimethylamino)benzoic acid there may be mentioned a) catalytic hydrogenation of 3-nitrobenzoic acid in methanol in the presence of Pd—Fe catalyst followed by methylation with formaldehyde as disclosed in Xiangtan Daxue Ziran Kexue Xuebao (1992) 14(4) 52-4, Chemical Abstract volume 120, 133965 and in Huaxue Shiji (1993) 15(5) 316, Chemical Abstract volume 120,106485.

b) catalytic hydrogenation of 3-nitrobenzoic acid in ethanol in the presence of 5% Pd—C at 90–95 C followed 40 minutes later by reductive methylation using 37% aqueous solution of formaldehyde giving 3-(N,N-dimethylamino)benzoic acid in 93% yield as disclosed in JP 57081444, Chemical Abstracts volume 97, 181976.

c) catalytic hydrogenation of 3-nitrobenzoic acid in methanol containing Pd—C and acetic acid followed by reductive methylation of the resulting 3-aminobenzoic acid as disclosed in DE 2930616.

d) catalytic hydrogenation of 3-nitrobenzoic acid in water followed by reductive methylation using 37% aqueous solution of formaldehyde added in 3 portions at 45 minute intervals to give 3-(N,N-dimethylamino) benzoic acid in 98% yield as disclosed in JP52071424, Chemical Abstracts volume 87, 151861.

However, the methods documented are disadvantageous for industrial manufacture in some part of their processing, namely the use of relatively large quantities of solvent or the use of less common catalysts such as a mixed metal catalyst that are more problematic during metal separation and recovery. Additionally, the procedures that have been described where the reaction is carried out in an essentially aqueous medium have no control over the pH of the reaction medium thus leading to unwanted side reactions and the formation of by-products.

It is, therefore, an object of the invention to provide a method of producing 3-(N,N-dimethylamino)benzoic acid of high purity and in high yield by the reductive methylation of an alkali metal salt or ammonium salt of 3-aminobenzoic acid. The reductive methylation is carried out within a carefully controlled temperature range and in an aqueous or aqueous/methanolic medium by the continuous controlled addition of formaldehyde, either as a water or methanol solution. The hydrogenation is carried out in the presence of a buffering agent such that the pH of the reaction mass is controlled thus limiting the formation of unwanted by-products.

The invention thus provides an improvement in a method of producing 3-(N,N-dimethylamino)benzoic acid, the improvement being the use of a buffering agent to control the pH of the reaction mass and the continuous and controlled addition of formaldehyde whilst increasing the reaction temperature within a defined temperature range.

Accordingly the present invention provides a process for the preparation of 3-(N,N-dimethylamino)benzoic acid which comprises subjecting an aqueous solution of an alkali metal salt or ammonium salt of 3-aminobenzoic acid to reductive methylation in the presence of a supported transition metal catalyst, by the controlled and continuous addition of a solution of formaldehyde over a period of 0.5 to 20 hours with a hydrogen pressure between 1 bar and 40 bar and with the temperature of the reaction mass gradually raised during the reduction, the reaction being carried out within the temperature range of 20° C. to 120° C., and wherein a buffering agent is added such that the pH of the reaction mass after reductive methylation is from 6.5 to 9.5.

As alkali metal salts there may be mentioned lithium, sodium and potassium of which the sodium salt of 3-aminobenzoic acid is preferred.

As transition metal catalysts there may be mentioned, but not limited by, palladium and platinum. The catalyst may or may not be further treated to affect the activity of the catalyst and may or may not be admixed with other metals. From the choice of catalysts available palladium is preferred.

The support for the catalyst is a contributing factor in the final performance of the catalyst. It has been found that carbon is a suitable support although this is not necessarily a limiting factor.

The temperature range at which the reductive methylation step is carried out may be from 20 C to 120 C but preferably from 20 C to 50 C. Although the reductive methylation may be carried out at a particular temperature it has been found that it is advantageous if the temperature at the start of the reductive methylation is from 20 C to 35 C and that during the addition of the formaldehyde the temperature is raised such that at the end of the formaldehyde addition the temperature is from 40 C to 60 C, preferably 50 C.

The formaldehyde may be used as an aqueous solution or as a methanolic solution. It is advantageous that the formaldehyde solution is added in a controlled and continuous manner over a period of 0.5–20 hours, preferably 1–4 hours, under the temperature conditions previously described.

The hydrogen pressure at which the reductive methylation step is carried out may be from 1 bar to 40 bar but preferably from 25 bar to 35 bar which gives a slightly better quality.

As buffering agents there may be mentioned, but not limited by, water soluble carboxylic acids such as formic acid, acetic acid, tartaric acid, citric acid and ascorbic acid. The quantity required is dependent upon the acid used but is such that at the end of the reductive methylation step the pH of the reaction mass is within the range 6.5 to 9.5 and preferably within the range 7.5 to 8.5.

The 3-aminobenzoic acid salt may be prepared in situ by the catalytic hydrogenation of a salt of 3-nitrobenzoic acid. This may be carried out using a supported transition metal as catalyst at a temperature of from 20° C. to 120° C. and a hydrogen pressure of from 1 bar to 40 bar.

The buffering agent required for the reductive methylation may be added prior to the reduction of the 3-nitrobenzoic acid if desired.

The temperature range at which the reduction of the nitro group to the amino group is carried out may be from 20 C to 120 C and the hydrogen pressure from 1 bar to 40 bar, preferably from 80° C. to 100° C., preferably from 25 bar to 35 bar. This reduction step is highly exothermic and the chosen conditions may be dictated by the type of equipment used and the cooling efficiency associated with the equipment. It has been found that the conditions of about 90 C and 30 bar hydrogen pressure are well suited.

After the reduction of 3-nitrobenzoic acid to 3-aminobenzoic acid the reaction mass may be cooled to a temperature <50 C and preferably to a temperature from 20 C to 35 C.

The invention will now be described by way of example but should not be considered as being limited to the examples herein.

EXAMPLE 1

Water (55.0 g), 3-nitrobenzoic acid (146.4 g; 0.876 mole) and sodium hydroxide (34.9 g; 0.872 mole) as a 47% aqueous solution are charged to a suitable laboratory pressure reactor. The pH is adjusted to 6.5 and the reaction mass temperature to 90 C. The volume is adjusted to 310 ml with water at 90 C. Citric acid (2.0 g) and 5% Pd/C (2.24 g) are then added and the reaction mass hydrogenated at 30 bar hydrogen pressure at a temperature of 90 C.

The reaction mass is cooled to 35 C when hydrogen uptake has ceased. A 50% methanolic solution of formaldehyde (111.5 g; 1.858 mole) is then added in a controlled and continuous manner during a period of 2 hours whilst raising the temperature from 35 C to 50 C. After complete addition the reaction mass is maintained at 50 C until hydrogen uptake has ceased. The reaction is filtered to recover the catalyst. The pH of the reaction mass was 8.1 and analysis showed a conversion from 3-nitrobenzoic acid to 3-(N,N-dimethylamino)benzoic acid of 99% theory.

EXAMPLE 2

The reaction is carried out by a similar procedure to Example 1 except that the citric acid is replaced by acetic acid and the temperature raised from 25 C to 50 C during the reductive methylation step. The yield and quality of the 3-(N,N-dimethylamino)benzoic acid is comparable with Example 1.

EXAMPLE 3

The reaction is carried out by a similar procedure to Example 2 except that the reductive methylation is carried out at 9 bar hydrogen pressure. The resulting 3-(N,N-dimethylamino)benzoic acid contains a higher level of impurities but is suitable for conversion to of 3,3-bis[4-(N,N-dimethylamino)phenyl]-6-N,N-dimethylamino-phthalide.

We claim:

1. A process for the preparation of 3-(N,N-dimethylamino)benzoic acid which comprises subjecting an aqueous solution of an alkali metal salt or ammonium salt of 3-aminobenzoic acid to reductive methylation in the presence of a supported transition metal catalyst, by the controlled and continuous addition of a solution of formaldehyde over a period of 0.5 to 20 hours with a hydrogen pressure between 1 bar and 40 bar and with the temperature of the reaction mass gradually raised during the reduction, the reaction being carried out within the temperature range of 20° C. to 120° C., and wherein a buffering agent is added such that the pH of the reaction mass after reductive methylation is from 6.5 to 9.5.

2. The process of claim 1 in which the alkali metal salt of 3-aminobenzoic acid is the lithium salt, sodium salt or potassium salt.

3. The process of claim 1 in which the transition metal catalyst is supported palladium or platinum.

4. The process of claim 1 when is carried out at from 20° C. to 50° C.

5. The process of claim 1 in which the formaldehyde is used as an aqueous solution, or methanolic solution.

6. The process of claim 1 in which the hydrogen pressure at which the reductive methylation step is carried out is from 25 bar to 35 bar hydrogen pressure.

7. The process of claim 1 in which the buffering agent is chosen such that the pH of the final reaction mass is from pH 7.5 to pH 8.5.

8. The process of claim 1 in which the 3-aminobenzoic acid salt is prepared in situ by the catalytic hydrogenation of a salt of 3-nitrobenzoic acid.

9. The process as claimed in claim 8 in which the reduction of the nitro group to the amino group is carried out at a temperature from 20° C. to 120° C. and at a hydrogen pressure of from 1 bar to 40 bar.

* * * * *